(12) United States Patent
Melrose

(10) Patent No.: US 7,438,899 B2
(45) Date of Patent: Oct. 21, 2008

(54) CHEMOTHERAPEUTIC COMPOSITIONS

(75) Inventor: Graham John Hamilton Melrose, Nedlands (AU)

(73) Assignee: Chemeq Ltd., Western Australia (AU)

( * ) Notice: Subject to any disclaimer, the term of this patent is extended or adjusted under 35 U.S.C. 154(b) by 317 days.

(21) Appl. No.: 10/792,867

(22) Filed: Mar. 5, 2004

(65) Prior Publication Data

US 2004/0170599 A1    Sep. 2, 2004

Related U.S. Application Data

(62) Division of application No. 08/952,648, filed as application No. PCT/AU96/00328 on May 30, 1996, now Pat. No. 6,723,336.

(30) Foreign Application Priority Data

May 30, 1995    (AU) .................................... PN3276

(51) Int. Cl.
*A61K 31/74*    (2006.01)
(52) U.S. Cl. .................................... 424/78.01; 514/693
(58) Field of Classification Search .................. None
See application file for complete search history.

(56) References Cited

U.S. PATENT DOCUMENTS

| | | | |
|---|---|---|---|
| 3,240,605 A | 3/1966 | Legator | |
| 3,711,290 A | 1/1973 | Miller | |
| 3,934,007 A | 1/1976 | Gussin et al. | |
| 3,936,423 A | 2/1976 | Randazzo | |
| 4,438,258 A | 3/1984 | Graham | |
| 4,460,560 A | 7/1984 | Tokes et al. | |
| 4,783,336 A | 11/1988 | Margel et al. | |
| 6,723,336 B1 * | 4/2004 | Melrose ....................... | 424/438 |

FOREIGN PATENT DOCUMENTS

| AU | 10864/88 A | 7/1988 |
|---|---|---|
| DE | 24 30 366 | 1/1975 |
| WO | WO 84/02270 A1 | 6/1984 |
| WO | WO 88/04671 * | 6/1988 |

OTHER PUBLICATIONS

Lacoste et al. "Gamma-Photo- and Thermally-Initiatd Oxidation of Linear Low Density Polyethylene: a Quantitative Comparison of Oxidation Products" Journal of Polymer Science, A. vol. 30, 493-500 (1992).*

T. A. Connors et al., Eur. J. Cancer, vol. 31A, No. 7/8, pp. 1373-1378 (1995).
S. Margel et al., J. Polymer Science: Polymer Chem. Ed., vol. 22, pp. 145-158 (1984).
Hodnett et al., Journal of Medicinal Chemistry, vol. 17, No. 12, pp. 1335-1337 (1974).
Paulicks, Nutritive Efficacy of Polyacrolein—Piglets Agrobiological Research, 48 (314), pp. 241-247 (1995).
Molt, Agribiological Research, 48, 3-4, 1995.
Facsimile from The Univeristy of New South Wales to Agribiological Research, dated Apr. 9, 2001, and Response from J. Saueriander's dated Apr. 11, 2001.
Facsimile dated Apr. 9, 2001, from Australian Patent Firm to J. ft Sauerlander's Verlag, regarding Agribiological Research article (in German with English translation).
Letter from J. Sauerlandews Verla to Australian Patent Firm dated Nov. 30, 2001 (with English translation).

* cited by examiner

*Primary Examiner*—Michael G. Hartley
*Assistant Examiner*—Eric E. Silverman
(74) *Attorney, Agent, or Firm*—Birch, Stewart, Kolasch & Birch, LLP

(57) ABSTRACT

The present invention relates to the treatment of gastrointestinal disease and/or cancer, and a method of weight gain, via the ingestion of polymeric compositions in humans, animals or birds in need of said treatment. The invention provides methods for the treatment of cancer, the treatment and/or prevention of gastrointestinal disease and/or infection and/or diarrhoea, and a method for increasing weight gain in humans, animals or birds comprising administering to said humans, animals or birds an effective amount of a pharmaceutical or veterinary composition, or feed additive, comprising an effective amount of a polymer and/or copolymer, having the repeating polymeric unit (I),

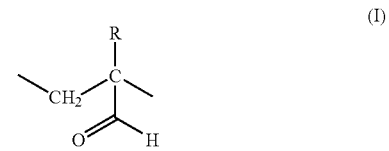

(I)

wherein R is H or alkyl, usually $C_1$ to $C_4$, or this unit in hydrated, hemiacetal or acetal form, together with a pharmaceutically or veterinarally acceptable carrier, diluent, adjuvant, excipient and/or controlled release system.

12 Claims, No Drawings

CHEMOTHERAPEUTIC COMPOSITIONS

CROSS-REFERENCE TO RELATED APPLICATIONS

The present application is a Rule 53(b) divisional of U.S. application Ser. No. 08/952,648 filed Nov. 24, 1997 now U.S. Pat. No. 6,723,336 which is the national phase of PCT International Application No. PCT/AU96/00328 filed May 30, 1996, which claims priority on Australian Application No. PN 3276 filed May 30, 1995. The entire contents of PCT Application No. PCT/AU96/00328 is hereby incorporated by reference.

TECHNICAL FIELD

The present invention relates to the treatment of gastrointestinal disease, and/or cancer, and a method of weight gain, via the ingestion of polymeric compositions in humans, animals or birds in need of said treatment.

BACKGROUND ART

Under the conditions of intensive pig-rearing, post weaning colibacillosis is ubiquitous. For example, intensive pig-rearing is used throughout Europe, the United States and Australia. For example, in the United States, post-weaning colibacillosis is the most common cause of mortality in the weaner pig (Leman et al., 1986). The disease is associated with the proliferation of Escherichia coli bacteria in the anterior small intestine after weaning, and gives rise to either death, or the young weaner failing to make normal weight-gains. Other microbiological diseases are common and often accompany colibacillosis in pigs as well as in other animals in intensive rearing conditions, especially poultry.

In the past, attempts have been made to control disease by the ingestion of antimicrobial compositions or by vaccination, neither of which has proved entirely effective.

The rationale behind the lack of success surrounding ingestion of antimicrobial compositions has been the fact that proteinaceous feedstuffs and the contents of the gastrointestinal tract present a reactive and hazardous environment to any chemotherapeutic agent and hence, in vitro active antimicrobial agent will often not be effective when used in vivo within the gastrointestinal tract.

Further, to be antimicrobially effective in a practical way, there is often the restrictive demand that the gastrointestinal disease controlling agent should reasonably maintain the very low microbiological content in the duodenum, yet the very high content in the lower parts of the intestine.

As well, it does not follow that even in vivo effective antimicrobials will give weight-gains, since it is common that even a cocktail of several such commercially used antimicrobials only gives rise to variable, partial or even negative relative weight-gains over control animals.

Accordingly, there is a need for improvements in the prevention and/or treatment of disease via ingestion of antimicrobial compositions in humans and/or animals and/or birds in need of said treatment. Furthermore, there is the need for the attainment of weight gains of said humans and/or animals and/or birds undergoing said treatment.

The present invention provides polymers and/or copolymers preferably derived from acrolein and having the polymeric repeating unit:

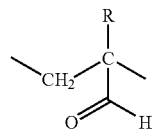

wherein R is H or alkyl, usually $C_1$ to $C_4$ or this unit in hydrated, hemiacetal or acetal form and illustrated non-comprehensively of all possible structures, by the following formulae:

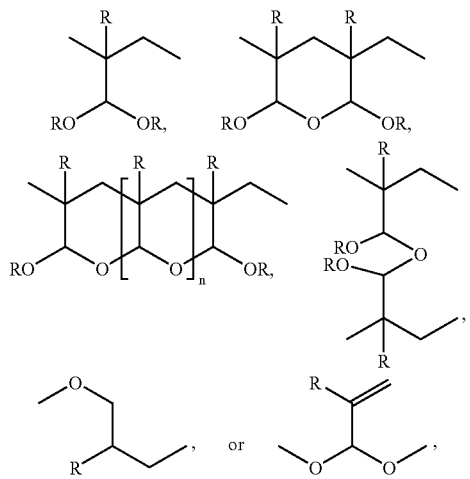

wherein n is one or more and R is as defined above; hereinafter referred to as the "Subject Polymers", as broad spectrum in vivo antimicrobials and/or anti-cancer agents suitable for treatment by the oral route.

It is known that the rate of passage of molecules across membranes has an inverse relationship to their molecular weights. Thus, it is widely and generally accepted in the art that molecules taken by the oral route and having molecular weight <1000, will have their passage across the gut so restricted, and consequently any potential toxicity will be effectively minimized.

The Subject Polymers, being aldehydic, are especially reactive with protein. (In fact, in microbiological assays, the routine and facile method of quenching/destroying the activity of the Subject Polymers is to add protein.) Hence, the Subject Polymers would not be expected to exhibit significant microbiological activity in the intestine, especially in the presence of proteinaceous feed.

Therefore, the present invention provides a method of prevention and/or treatment of gastrointestinal disease in humans, animals or birds resulting from the microbial infection of the gastrointestinal tract, and a method for increasing weight gain in humans, animals or birds having gastrointestinal disease and/or infection, comprising administering an effective amount to said humans, animals or birds of a pharmaceutical composition or feed additive, comprising an effective amount of the Subject Polymers together with a pharmaceutically or veterinarally acceptable carrier, diluent, adjuvant, excipient or controlled release system.

OBJECT OF THE INVENTION

It is an object of the present invention to provide methods for the prevention and treatment of dysfunctional/pathological states in a human, animal or bird, especially, those states within the gastrointestinal tract associated with colibacillosis, diarrhea, mortality and/or reduced weight gains.

DISCLOSURE OF THE INVENTION

The present invention is based upon a series of discoveries herein:

First, it has now been discovered that the Subject Polymers, being of high molecular weight are inhibited in passage through biological membranes, and have facilitated applications in the gastrointestinal tract, since passage through the gut and into the bloodstream to potentially cause toxicity is minimized. In particular, it has been discovered that the Subject Polymers have molecular weights >1000, and generally have molecular weights >2000, which effectively minimize their passage across the intestinal membranes and as a result, it has been found herein that whilst the Subject Polymers exhibit toxicity following intra-venous injection, they exhibit no toxicity when administered orally. Hence it has been discovered that the Subject Polymers have minimized toxicities and that they have associated advantages when used for chemotherapeutic purposes, in any species having gut membranes, for example, humans, animals or birds.

Generally, the Subject Polymers formed by ionic initiation/catalysis are more hydrophilic than those formed by free radical initiation/catalysis, and hydrophilicity of the Subject Polymers may generally be increased by inclusion within them of hydrophilic groups, especially carboxyl groups, or of hydrophilic monomers, especially acrylic acid. Particularly, carefully heating the Subject Polymers formed by ionic initiation/catalysis with ample air from room temperature to up to 100° C., and preferably up to between 80-85° C., produces the Subject Polymers having 0.1-5 moles of carboxyl groups/kg, aqueous soluble at the pH of the duodenum especially, and preferred for the applications in gastrointestinal tracts described and envisaged herein.

The Subject Polymers have the following properties:

The Subject Polymers have an unusually broad in vivo antimicrobial profile, providing a method of treatment of gastrointestinal disease in humans, animal or birds.

It has been shown that the Subject Polymers provide increased weight gains in humans, animals or birds.

It has also been shown that the Subject Polymers are in vivo anti-cancer agents.

According to a first embodiment of the invention there is provided a method of in vivo cancer treatment in humans, animals or birds comprising administering to said humans, animals or birds an effective amount of a pharmaceutical or veterinary composition or feed additive, comprising an effective amount of polymers and/or copolymers having the repeating polymeric unit:

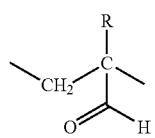

wherein R is H or alkyl, usually $C_1$ to $C_4$, or this unit in hydrated, hemiacetal or acetal form and illustrated non-comprehensively of all possible structures, by the following formulae:

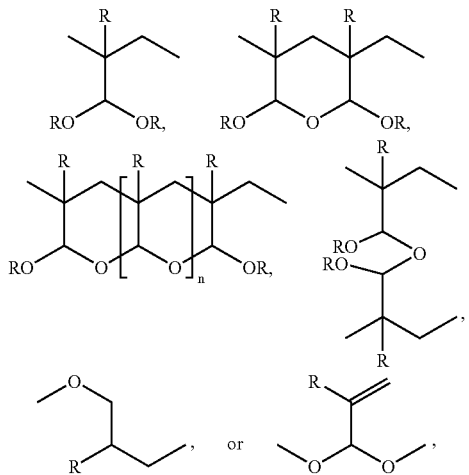

wherein n is one or more and R is as defined above; together with a pharmaceutically or veterinarally acceptable carrier, diluent, adjuvant, excipient and/or controlled release system.

According to a second embodiment of the invention there is provided a method for the treatment and/or prevention of gastrointestinal disease and/or infection and/or diarrhea in humans, animals or birds resulting from a microbial infection of the gastrointestinal tract in said humans, animals or birds, comprising administering to said humans, animals or birds an effective amount of a pharmaceutical or veterinary composition or feed additive, comprising an effective amount of a polymer and/or copolymer as defined in the first embodiment of the invention, together with a pharmaceutically or veterinarally acceptable carrier, diluent, adjuvant, excipient and/or controlled release system.

According to a third embodiment of the invention there is provided a method of increasing weight gain in humans, animals or birds having cancer and/or gastrointestinal microbial disease and/or infection, in said humans, animals or birds, comprising administering to said humans, animals or birds an effective amount of a pharmaceutical or veterinary composition or feed additive, comprising an effective amount of a polymer and/or copolymer as defined in the first embodiment of the invention, together with a pharmaceutically or veterinarally acceptable carrier, diluent, adjuvant, excipient and/or controlled release system.

In terms of the Subject Polymers being a prevention and/or treatment for gastrointestinal disease, it has now been shown that farm-piglets given the Subject Polymers ad libitum in their drinking water, have reduced numbers of diarrhea days and lower counts of E. coli in their excreta. Moreover, the effect as proposed, is markedly greater than the partial effect exhibited by the administration of commercial antimicrobial agents together with vaccination.

In addition, it has now been discovered that the Subject Polymers in a polymeric controlled-release system as well as leading to fewer diarrhea days in the animal, also gave rise to extraordinarily high weight-gains. As exemplified in Example 17, piglets displayed lower mortality, and weight gains of some 46% above control piglets.

Therefore, it is proposed that the Subject Polymers should be provided as an additive to the animal's solid feed, in the form of a polymeric controlled-release system, since then, the Subject Polymers would be released slowly and mainly in the duodenum. Further, it is now proposed that having the Subject Polymers in a controlled-release system will reduce any destructive chemical reaction between the Subject Polymers and either constituents of the gastro-intestinal tract or the proteinaceous feed, especially during the essential pre-heat sterilization of the feed. Furthermore, any rejection by the animal due to taste, will be reduced.

When using the Subject Polymers for the treatment of disease and/or infection in humans, animals or birds in need of treatment, for example in piglets having diarrhea associated with colibacillosis, it is preferred to begin dosing immediately after weaning and to always continue for the next 5 days, sometimes for the next 30 days, but preferably at least for the next 15 days after weaning; at any time that such symptoms of diarrhea are observed. Treatment in a controlled-release form is preferred and containing theoretically 5%-50% w/w Subject Polymers but preferably, 20%-30% w/w. Preferably the controlled-release form/pellet is added to the feed, either during production of the feed or during feeding such that the feed contains 1%-20% w/w and preferably 2%-8% w/w of pellet. If for example a piglet of 5 kg daily eats 500 g of feed with 4% w/w controlled-release pellet containing 25% w/w Subject Polymers—this calculates to a dose rate of Subject Polymers of 1000 mg/kg(liveweight)/day; in a controlled-release form a dose rate of 50-5000 mg/kg/day is practical but 500-2500 mg/kg/day is preferred. Smaller dose rates of 25-500 mg/kg/day should be used when the Subject Polymers are given in a non-controlled-release form. Dose protocols and rates are similar for other microbiological infections and for cancer.

Both the in vivo antimicrobial activity in the presence of relatively huge quantities of reactive proteins in the gastro-intestinal tract, and the range of chemotherapeutic activities of the Subject Polymers, revealed herein, are surprising. Also, in unpublished work, the Subject Polymers have been found to exhibit significant anti-coagulant activities in human or a range of various animal bloods. This particular range of surprising in vivo activities suggests that unexpectedly, the Subject Polymers have such activities related to lectin-selectin-integrin type adsorptive inter-actions.

Compositions for administration in the method of the invention may be prepared by means known in the art for the preparation of compositions (such as in the art of veterinary and pharmaceutical compositions) including blending, grinding, homogenizing, suspending, dissolving, emulsifying, dispersing and where appropriate, mixing of the Subject Polymers together with selected excipients, diluents, carriers and adjuvants.

For oral administration, the pharmaceutical or veterinary composition may be in the form of tablets, lozenges, pills, troches, capsules, elixirs, powders, including lyophilized powders, solutions, granules, suspensions, emulsions, syrups and tinctures. Slow-release, or delayed-release, forms may also be prepared, for example in the form of coated particles, multi-layer tablets or microgranules.

It is preferred that the controlled release system comprises a pH-sensitive, crosslinked, water-absorbent pellet, which when wet is a gel.

Solid forms for oral administration may contain pharmaceutically or veterinarally acceptable binders, sweeteners, disintegrating agents, diluents, flavorings, coating agents, preservatives, lubricants and/or time delay agents. Suitable binders include gum acacia, gelatin, corn starch, gum tragacanth, sodium alginate, carboxymethylcellulose or polyethylene glycol. Suitable sweeteners include sucrose, lactose, glucose, aspartame or saccharine. Suitable disintegrating agents include corn starch, methylcellulose, polyvinylpyrrolidone, xanthan gum, bentonite, alginic acid or agar. Suitable diluents include lactose, sorbitol, mannitol, dextrose, kaolin, cellulose, calcium carbonate, calcium silicate or dicalcium phosphate. Suitable flavoring agents include peppermint oil, oil of wintergreen, cherry, orange or raspberry flavoring. Suitable coating agents include polymers or copolymers of acrylic acid and/or methacrylic acid and/or their esters, and/or their amides, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

Liquid forms for oral administration may contain, in addition to the above agents, a liquid carrier. Suitable liquid carriers include water, oils such as olive oil, peanut oil, sesame oil, sunflower oil, safflower oil, arachis oil, coconut oil, liquid paraffin, ethylene glycol, propylene glycol, polyethylene glycol, ethanol, propanol, isopropanol, glycerol, fatty alcohols, triglycerides or mixtures thereof.

Suspensions for oral administration may further comprise dispersing agents and/or suspending agents. Suitable suspending agents include sodium carboxymethylcellulose, methylcellulose, hydroxypropylmethyl-cellulose, polyvinylpyrrolidone, sodium alginate or cetyl alcohol. Suitable dispersing agents include lecithin, polyoxyethylene esters of fatty acids such as stearic acid, polyoxyethylene sorbitol mono-or di-oleate, -stearate or -laurate, polyoxyethylene sorbitan mono- or di-oleate, -stearate or -laurate and the like.

The emulsions for oral administration may further comprise one or more emulsifying agents. Suitable emulsifying agents include dispersing agents as exemplified above or natural gums such as gum acacia or gum tragacanth.

According to a fourth embodiment of the invention there is provided a method of producing pellets, the pellets comprising polymers and/or copolymers as defined in the first embodiment of the invention, together with a pharmaceutically or veterinarally acceptable carrier, diluent, adjuvant, excipient and/or controlled release system, mainly within a polymeric matrix. The method comprising adding a polymeric matrix to a solution, suspension or emulsion of the polymers and/or copolymers as defined in the first embodiment of the invention.

According to a fifth embodiment of the invention there is provided a method of producing pellets or like solid composition, the pellets comprising polymers and/or copolymers as defined in the first embodiment of the invention, mainly within a polymeric matrix, said method as defined in the fourth embodiment of the invention and comprising the steps of:

(i) dissolving said polymers and/or copolymers in an aqueous alkaline or basic solution;

(ii) neutralizing said solution with acid;

(iii) adding to said neutralized solution insoluble, crosslinked, absorbent polymers of acrylic acid and/or copolymers of acrylamide and acrylic acid, to form wet, swollen pellets; and (iv) optionally, wholly or partially drying said wet swollen pellets.

The so-formed wet, swollen pellets may be used either wet, partially dried or wholly dried, as an additive to, for example, animal feed. This system is further designed so that the carboxyl-containing groups of the outer polymeric matrix cause the Subject Polymers to remain essentially contained within the matrix when in the acidic environment of the stomach. However, in the alkaline environment of the duodenum, the carboxyl groups of the matrix become ionized and mutually-repelling, and the pellet rapidly swells to allow the Subject Polymers, aided by repulsion among their own ionic groups, to be excluded by a diffusion process, approximately matching the speed of passage of feed through the duodenum.

In this invention, the term, "controlled release system" is used in the same context as that in, and includes the same range of examples as quoted in "Controlled Drug Delivery" (Robinson & Lee, 1987). Many other pH-sensitive controlled-release systems which are known in the art (Robinson and Lee, 1987) may be substituted for the polymer of acrylic acid or copolymer of acrylamide and acrylic acid. For example, soluble and anionic or insoluble, cross-linked and anionic, cellulosic systems or soluble and anionic, or insoluble, cross-linked and anionic polymers derived from any generic acrylic acid and/or its derivatives. Such cross-linked and insoluble polymers are preferred since they swell and also, are less likely to be metabolized.

In summary, the compositions described herein may be used to control cancer and/or microbiological disease and especially result in greater weights of humans, animals or birds having gastrointestinal infections. The invention is applicable in humans, animals or birds having microbiological diseases of the gastrointestinal tract for example, *Escherichia coli*. A preferred use is to bring about greater weights in newly-weaned piglets having diarrhea and associated with the proliferation of *Escherichia coli* bacteria in the anterior small intestine. The invention may be applicable in humans having gastrointestinal disease, for example, from *Staphylococcus aureus* and/or *Helicobactor pylori* bacteria.

The invention will now be described with reference to specific Examples, which should not be construed as limiting on the scope thereof.

EXAMPLES 1 TO 13

Preparations and Structures of Subject Polymers

EXAMPLE 1

(a) Using a free radical initiator/free radical catalyst: 9.64 g distilled acrolein and 25 g methanol were placed in a 100 ml round bottom flask and purged with nitrogen. 0.525 g benzoyl peroxide was added and the solution stirred under nitrogen at 60° C. The reaction was allowed to continue for a total of ca. 88 hours. After this time the reaction solution had become strongly yellow in color and had a solids content of 30.5%. $^{13}$C-NMR (300 MHZ) δ(relative to $d_4$-methanol at 49.00): 33.27 (CH); 33.53 (CH); 33.79 (CH); 33.87 ($CH_2$); 37.03 (CH); 37.29 (CH); 37.54 (CH); 37.64 ($CH_2$); 97.15 (CH); 103.37 (CH); 104.34 (CH); 139.36 (CH); 139.78($CH_2$); 196.72 (CH). The $^{13}$C-NMR spectrum shows some residual acrolein with the aldehyde carbon at δ196.72 and the vinylic $CH_2$ and CH at δ139.78 and δ139.36, respectively; apart from the δ196.72 (CH) resonance absorption, there was no other attributed to —CHO. The spectrum is consistent with polymeric acrolein consisting of fused tetrahydropyran rings and some free dihydroxy methyl groups. The rings exist in either the boat or chair conformations giving rise to more chemical shifts than may be expected.

Typically, as an indication of molecular weight, the polyacrolein was found to have a retention time which was shorter than that of polyethyleneglycol 2,000 on a Porasil GPC 60 Angstrom column using a Waters Associated Model ALC/GPC 204 liquid chromatograph fitted with a differential refractometer R401.

(b) Using an ionic initiator/catalyst: 1.6 g distilled acrolein was made up to 20 ml with demonized water in a 200 ml beaker and then, ca. 0.5 ml of 0.2M sodium hydroxide added with stirring to pH ca. 10-11. The solution became cloudy and a white precipitate began to form. The contents were stirred for a further 2 hours and then filtered. The precipitate was washed thoroughly with demonized water until the filtrate was neutral. The product may be carefully heat-dried in contact with ample air, initially at ambient temperatures and then at temperatures up to about 100° C. Alternatively, as in this case, the product may be dried under vacuum to a white-pale yellow, fine powder; dissolved in methanol, and it may be evaporated down to dryness and then again, dissolved in methanol or other solvents. Often, the Subject Polymers have 0.1-5 moles of carboxyl groups/kg and were found to have GPC retention times which were mainly shorter than that of polyethylene glycol 2,000. $^{13}$C-NMR (300 MHz) δ(relative to $d_4$-methanol at 49.00): 19-31 ($CH_2$); 35.95 ($CH_2$); 37-42 (CH); 62-73 ($CH_2$); 73-81 (CH); 92-95 (CH); 96-103 (CH); 114-120 ($CH_2$); 134-141 (CH); 196.0 (CH).

In experiments using in each case, 2 groups of 10 Swiss white mice (treated and control, respectively) it was found that solutions of the Subject Polymers in aqueous triethanolamine adjusted to pH 8, had an acute intra-venous toxicity of 320 mg/kg, and acute oral toxicity of >5000 mg/kg (no deaths nor abnormal signs were apparent over 14 days).

EXAMPLE 2

6.489 g distilled acrylic acid, 0.56 g distilled acrolein and 15 g methanol were placed in a 50 ml round bottom flask and purged with nitrogen. 0.33 g benzoyl peroxide was added and the solution stirred under nitrogen at 60-65° C. The reaction was continued for ca. 66 hours. After this time the contents of the flask had become very viscous, having a solids content of 57.7% (indicating 100% conversion).

A sample of the viscous material was placed on a petri dish and dried on a hot plate to remove solvent. Drying was completed in an oven at 80° C. and a transparent, slightly yellow colored polymer was obtained. The copolymer is completely soluble in warm water (ca. 50° C.) and once dissolved remains so, even on cooling the solution.

In order to ensure that the solids obtained were polymeric, a simple dialysis experiment was performed: 10 g of an aqueous solution containing 0.65% solids was placed in a dialysis tube. This was irrigated with water continuously for ca. 66 hours. The solution in the dialysis tube was then recovered and the solids content determined at 0.68%. Since the solids were completely retained and the lower limit for solids penetration through the dialysis tube is 2000 mwt, it is concluded that the solids are polymeric.

EXAMPLE 3

2.8 g of acrolein diethyl acetal was placed in a 100 ml round bottom flask and the contents purged with nitrogen. A solution of 0.216 g potassium persulphate in 7.5 g water was added with stirring, under nitrogen. The flask was placed in an oil bath at 60-70° C. and stirred for ca. 20 hours. A yellow solid was recovered and dried at 50° C.; weight 0.915 g.

EXAMPLE 4

4 g distilled acrylic acid, 4.81 g acrolein diethyl acetal and 15 g methanol were placed in a 50 ml round bottom flask and purged with nitrogen. Then 0.3 g benzoyl peroxide was added and stirring continued under nitrogen at 60-65° C. for 70 hours (solids determination indicated a 50% conversion). $^{13}$C-NMR (300 MHz) δ(relative to $d_4$-ethanol at 49.00): 15.58 ($CH_3$); 18.31 ($CH_3$); 35.52 ($CH_2$); 36.24 ($CH_2$); 37.07 ($CH_2$); 42.36 (CH); 42.85 (CH); 58.32 ($CH_2$); 130.00 (CH); 131.57 ($CH_2$); 178.51 (CH).

EXAMPLE 5

3.8 g of acrolein diethyl acetal, 3.3 g vinyl pyrrolidone and 10 g methanol were placed in 50 ml round bottom flask and thoroughly purged with nitrogen. 0.71 g azobisisobutyronitrile was added and the flask heated in an oil bath at 60-65° C., with stirring under nitrogen for 72 hours when the conversion was 44%. The copolymer was found to be soluble in methanol.

EXAMPLE 6

In a similar technique to the above, 3.9 g acrolein diethyl acetal, 1.16 g acrylic acid, 7.5 ml water and 0.216 g potassium persulphate were heated under nitrogen, with stirring in an oil bath at 60-70° C. for ca. 24 hours when a white waxy material was recovered; it was insoluble in water, but swelled in methanol, acetone, tetra-hydrofaran or methyl ethyl ketone.

EXAMPLE 7

A similar result was achieved through heating and stirring in the usual way to the above: 14.5 g methanol, 3.62 g distilled acrolein, 1.21 g distilled acrylic acid and 0.265 g benzoyl peroxide. After 40 hours the conversion was 40%.

EXAMPLES 8-11

A 50:50 mixture of monomers was treated as follows: 2.35 g distilled acrolein, 2.88 g distilled acrylic acid and 14.5 g methanol were placed in a 50 ml round bottom flask and flushed with nitrogen. 0.2625 g benzoyl peroxide was added and after heating at 60-70° C. for 48 hours the conversion was 70%. The polymer swelled in methanol but was insoluble in water.

Similar preparations were achieved with different ratios of the monomers acrolein: acrylic acid namely, 30:70 (Example 9), 10:90 (Example 10), 2.5:97.5 (Example 11). The products from Examples 10 and 11 were soluble in water and retained by dialysis tubing of exclusion 2,000 mwt.

EXAMPLE 12

In a similar preparation to the above, 42% conversion was achieved of a polymer which swelled in methanol or water, from 1.8 g acrolein, 3.3 g vinyl pyrrolidone and 0.071 g azobisisobutyronitrile.

EXAMPLE 13

30 mg benzoyl peroxide was added to a solution of 1.02 g polyethyleneglycol acrylate and 0.5 ml acrolein in 5 ml methanol. The mixture was stirred and heated to reflux for 48 hours and gave 90% conversion; the residual oil (1.2 g) was chromatographed on Sephadex LH-20 (18 g) in methanol. The structure of the resulting polymer was confirmed by NMR analysis.

EXAMPLE 14

Young adult female mice were inoculated intra-peritoneally with $2.3 \times 10^6$ Ehrlich ascites tumour cells and one week later, those mice with swollen abdomens were selected for further experimentation: 15 of such mice were treated twice a day for three days and 15 once a day for the next three days, with intra-peritoneal injections of the Subject Polymers in 0.5% aqueous sodium carbonate at a dose rate of 150 mg/kg mouse; a control group of 15 mice having Ehrlich ascites tumour cells was treated with the sodium carbonate solution, only. All mice in both groups were then sacrificed, the peritoneal fluids were collected and the number of tumour cells counted:

| Control Group | | Treated Group | |
|---|---|---|---|
| Mouse Number | Peritoneal cells × $10^9$ | Mouse Number | Peritoneal cells × $10^9$ |
| 1 | 2.30 | 16 | 0.97 |
| 2 | 3.55 | 17 | 0.54 |
| 3 | 2.13 | 18 | 0.14 |
| 4 | 0.05 | 19 | 0.06 |
| 5 | 2.55 | 20 | 0.11 |
| 6 | 2.27 | 21 | 0.07 |
| 7 | 2.93 | 22 | 0.27 |
| 8 | 1.93 | 23 | 0.93 |
| 9 | 2.34 | 24 | 0.36 |
| 10 | 5.58 | 25 | 1.04 |
| 11 | 2.23 | 26 | 0.12 |
| 12 | 1.65 | 27 | 0.64 |
| 13 | 4.76 | 28 | 0.16 |
| 14 | 2.01 | 29 | 0.67 |
| 15 | 3.36 | 30 | 0.54 |
| | x = 2.64 | | x = 0.44 |
| | s = 1.31 | | s = 0.35 |

A test showed the control and treated groups to be different at greater than 99% confidence level.

EXAMPLE 15

The Subject Polymers were suspended/dissolved in the drinking water of piglets, at 0.1% w/v for the first 2-3 days and then at 0.05% w/v for the next 7 days; drinking was ad libitum; consumption of Subject Polymers was approximately 200 mg/kg of piglet/day.

Three groups of 28-day, newly-weaned piglets (mean weight 5.6 kg) were studied:

1. Treated with Subject Polymer, only;
2. Treated with prior vaccination protocol, only;
3. No treatment at all (control).

During the 14-day trial, in keeping with usual practice at the farm, those piglets which were observed during the daily inspection to have diarrhea, were given an injection of antibiotic.

| | Treatment: Subject Polymers | Treatment: Vaccination Only | No Treatment: Control |
|---|---|---|---|
| No. 28-day piglets in group | 15 | 19 | 10 |

-continued

| | Treatment: Subject Polymers | Treatment: Vaccination Only | No Treatment: Control |
|---|---|---|---|
| No. diarrhea days (mean/piglet) | 0.47 | 1.11 | 1.8 |
| No. injections of antibiotic (mean/piglet) | 0.6 | 2.53 | 4.6 |
| No. piglets with heavy E. coli in faeces, day 7 (mean/piglet) | 0.53 | 0.79 | 0.9 |
| Weight-gain, 14 days (mean %/piglet) | 33 | 32 | 37 |

EXAMPLE 16

In a typical small-scale experiment, Subject Polymers (35 g) were dissolved with stirring in water (638 g) containing sodium carbonate (19 g), and then the solution was immediately neutralized to pH 7.2 with 10% hydrochloric acid; Sucrose (32 g; sweetening agent) which may be discretionally included, was added with continued stirring and then either an absorbent polymer of acrylic acid (64 g; CARBOPOL 934, B.F. Goodrich, USA) or an absorbent copolymer of acrylamide-acrylic acid (64 g; ALCOSORB AB 3S, Allied Colloids, England) was added. The resulting swollen beads took-up the typically pale-yellow color of the Subject Polymers in solution. The beads/pellets may be used wet, but were typically, either partially or wholly dried at temperatures up to 45° C., before use. However, higher temperatures, up to about 90-100° C. may be used. On the basis of solid substances added, theoretically, the pellets contain approximately 25% w/w of Subject Polymers.

Two experiments were undertaken to assess the rate of release of the Subject Polymers at simulated pHs of the stomach and the duodenum, respectively. First, the above fully-dried beads (200 mg) were gently stirred in 0.1M hydrochloric acid (100 mL). An aliquot (10 mL) was periodically removed and diluted in excess 0.2M aqueous sodium bicarbonate; measurement of a peak near 265 nm indicated a maximum release, in 0.1M hydrochloric acid, of approximately 35% after about forty five minutes. Second, by contrast, a comparable experiment in 0.1M aqueous sodium bicarbonate solution revealed 35% release in about twenty minutes, and 90%-100% after three to five hours. These properties of the beads were unaffected by heating conditions which may be used commercially, to reduce microorganisms in feed (90° C./30 minutes).

EXAMPLE 17

In one experiment, two groups, each of ten newly-weaned 21-day-old pigs from a commercial piggery were given an oral dose of E. coli (50 mL; $10^9$ CFU/mL) of haemolytic E. coli, cultured from a field case of post-weaning colibacillosis. On the same day, one group of the pigs was given ad libitum feeding of 19% crude protein feed containing the wholly-dried beads/pellets sprinkled in the feed at the rate of 3.75% w/w of feed. The pellets contained theoretically, approximately 25% w/w of the Subject Polymers. Furthermore, a "No Treatment" group was given feed, only. Each pig consumed about 500 g of feed, daily. Swabs were taken of rectal faeces initially and then again, 48 hours after dosage with the E. coli. Three days after this regime (during which time two pigs of the untreated group died with acute secretory diarrhea), all remaining pigs were sacrificed and the E. coli estimated semi-quantitatively in sections of the duodenum (after swabbing the mucosa and then using a scale of 4 (highest) to 0 (lowest) within the usual microbiologists' dilution-strike technique on culture plates). Post-mortem examination did not reveal any gastric inflammation in any pig.

Scores for haemolytic E. coli in the rectal faeces of pigs in the two groups on the day of inoculation, and 48-hours later, and are illustrated in the following table:

| Initial | | 48 hours later | |
|---|---|---|---|
| No Treatment | Treatment | No Treatment | Treatment |
| 1 | 2 | 1 | 0 |
| 0 | 0 | 3 | 1 |
| 1 | 1 | 4 | 2 |
| 1 | 0 | 4 | 0 |
| 0 | 1 | 3 | 1 |
| 0 | 2 | 2 | 1 |
| 0 | 1 | 1 | 1 |
| 1 | 1 | 4 | 0 |
| 0 | 0 | 4 | 2 |
| 0 | 0 | 2 | 2 |
| Total 4 | 8 | 28 | 10 |

After 48 hours the number of haemolytic E. coli in the faeces of the pigs receiving the Subject Polymers was significantly less than that in the untreated pigs ($\chi^2=16.24$; p=>0.001).

Furthermore, the distribution of haemolytic E. coli in the upper (25%) and mid (50%) jejunum of the treated and untreated pigs, after sacrifice, is recorded below:

| 25% | | 50% | |
|---|---|---|---|
| No Treatment | Treatment | No Treatment | Treatment |
| 1 | 1 | 2 | 1 |
| 0 | 0 | 1 | 0 |
| 1 | 1 | 4 | 4 |
| 3* | 0 | 4* | 0 |
| 2 | 0 | 3 | 1 |
| 1 | 1 | 2 | 1 |
| 1 | 3 | 2 | 3 |
| 4 | 0 | 4 | 0 |
| 3* | 20 | 4* | 0 |
| 1 | 0 | 2 | 0 |
| Total 17 | 6 | 28 | 9 |

*Dead pigs

The treated pigs had significantly fewer haemolytic E coli than the untreated pigs, at both 25% site ($\chi^*=7.38$; p=<0.01) and the 50% site ($\chi^2=16.24$; p=<0.001).

Another experiment was executed identically, except for the fact that 15 newly-weaned pigs were in each group. The initial inoculation of E. coli in the experimental group was reduced to one-third of previously described, and the controlled-release pellets theoretically contained 20% w/w of the Subject Polymers. Observations of diarrhea days and weight gain were made of the pigs over 21 days. The results showed the treated group had statistically significant fewer diarrhea days and statistically significant (46%) greater weight-gain over the control group.

| Live Weight Gains and Days of Diarrhea | | |
| --- | --- | --- |
| Group | Control | Treated |
| Number | 15 | 15 |
| Mean Initial weight (kg), day 1 | 4.77 | 4.43 |
| Standard Error | 0.22 | 0.19 |
| Relative (%) | 100.00 | 92.00 |
| Mean Final weight (kg), day 21 | 6.63 | 7.31 |
| Standard Error | 0.35 | 0.36 |
| Relative (%) | 100.00 | 110.30 |
| Mean Daily gain (g), 0–21 days | 94.18 | 137.33 |
| Standard Error | 10.27 | 13.16 |
| Relative (%)* | 100.00 | 146.00 |
| Days of diarrhea** | 32 | 13 |

*t = 2.47; p = 0.02 (two tail)
**No diarrhea in any pig, after day 10.

REFERENCES

Leman, A. D., Straw, B., Glock, R. D., Mengeline, W. L., Penny, R. H. C. and Scholl, E. (1986). "Diseases of Swine", 6th Edition, Iowa State University Press.

Robinson, J. R. and Lee, V. H. L. (1987). "Controlled Drug Delivery". Marcell Dekker.

What is claimed is:

1. A method of treatment of a gastrointestinal dysfunction in a human, animal or bird wherein the gastrointestinal disfunction is a gastrointestinal disease, gastrointestinal infection or diarrhea resulting from a bacterial infection of the gastrointestinal tract comprising administering to said human, animal or bird a polymer of molecular weight of at least 1000 comprising:
   (i) a repeating unit selected from the group consisting of units of formula 1

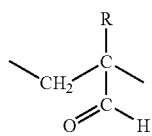

I wherein R is H or $C_1$ to $C_4$, alkyl and units derived from the unit of formula 1 selected from the group consisting of: the hydrated, hemiacetal and acetal forms thereof, and
   (ii) wherein the polymer has been prepared by a process of homopolymerization of acrolein by ionic initiation and heating the resulting acrolein homopolymer with ample air at a temperature of up to 100° C. whereby the polymer comprises carboxyl groups at a concentration of from 0.1 to 5 moles of carboxyl groups per kilogram of polymer.

2. The method according to claim 1 wherein said hydrated, hemiacetal and acetal forms are selected from the group consisting of the hydrated diol form, the hemiacetal or acetal form as formed from the condensation of the diol form with the aldehyde or diol form, the tetrahydropyran or fused tetrohydropyran formed from the condensation of the diol form, the aldol-Michael self-condensation form and mixtures thereof.

3. The method according to claim 1 wherein the gastrointestinal dysfunction is a bacterial disease or infection.

4. The method according to claim 3 wherein the bacterial disease or infection is caused by *E. coli*.

5. The method according to claim 3 wherein the bacterial disease or infection is cause by *H. pylori*.

6. The method according to claim 1 wherein the polymer is administered in the form of a feed.

7. The method according to claim 1 wherein the polymer is administered in drinking water.

8. The method according to claim 6 wherein the feed contains the polymer in a controlled release system.

9. The method according to claim 8 wherein the controlled release system releases the polymer or copolymer in an alkaline environment.

10. The method according to claim 1 wherein said polymer or copolymer is administered in an amount up to 5000 mg/kg/day.

11. The method according to claim 1 wherein said polymer or copolymer is administered in an amount from 50 mg/kg/day to 5000 mg/kg/day.

12. A method of treatment according to claim 1, wherein said heating the resulting acrolein polymer with ample air is conducted at a temperature in the range of from 80° C. to 85° C.

* * * * *